US010850073B2

(12) United States Patent
Pagoria et al.

(10) Patent No.: US 10,850,073 B2
(45) Date of Patent: Dec. 1, 2020

(54) DEVICES AND METHODS OF USE WITH DEVICES HAVING A RADIOPAQUE FILAMENT

(71) Applicant: Boston Scientific Scimed, Inc., Maple Grove, MN (US)

(72) Inventors: Douglas D. Pagoria, Forest Lake, MN (US); Joel T. Eggert, Plymouth, MN (US); James P. Rohl, Prescott, WI (US); Douglas Pennington, Stillwater, MN (US); Katherine L. Baldwin, Minneapolis, MN (US); James K. Cawthra, Jr., Ramsey, MN (US); Sarah M. Gruba, Vadnais Heights, MN (US); Daniel Shuey, Circle Pines, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 10 days.

(21) Appl. No.: 15/985,374

(22) Filed: May 21, 2018

(65) Prior Publication Data
US 2018/0333562 A1   Nov. 22, 2018

Related U.S. Application Data

(60) Provisional application No. 62/509,379, filed on May 22, 2017.

(51) Int. Cl.
*A61F 2/82*   (2013.01)
*A61M 25/09*   (2006.01)
(Continued)

(52) U.S. Cl.
CPC ............. *A61M 25/09* (2013.01); *A61B 6/487* (2013.01); *A61B 17/12122* (2013.01); *A61B 17/12136* (2013.01); *A61B 17/12172* (2013.01); *A61B 18/14* (2013.01); *A61B 18/1492* (2013.01); *A61F 2/90* (2013.01); *A61M 25/0012* (2013.01); *A61B 17/1227* (2013.01); *A61B 17/12177* (2013.01); *A61B 2017/00243* (2013.01);
(Continued)

(58) Field of Classification Search
CPC ........................................ A61F 2/82
See application file for complete search history.

(56) References Cited

U.S. PATENT DOCUMENTS

| 6,019,786 A | 2/2000 | Thompson |
| 6,340,367 B1 | 1/2002 | Stinson et al. |

(Continued)

FOREIGN PATENT DOCUMENTS

| DE | 202014102531 U1 | 7/2014 |
| DE | 202015105466 | 11/2015 |

(Continued)

OTHER PUBLICATIONS

International Search Report and Written Opinion for PCT/US2018/033717 dated Aug. 31, 2018 (13 pages).

*Primary Examiner* — Matthew W Schall

(57) ABSTRACT

The present disclosure relates generally to medical devices and methods for medical devices to be placed within a lumen of a patient, wherein the devices comprise one or more radiopaque filaments arranged with the devices and viewable to assist in placement and orientation of the devices with respect to the lumen.

20 Claims, 8 Drawing Sheets

(51) Int. Cl.
*A61B 6/00* (2006.01)
*A61M 25/00* (2006.01)
*A61B 17/12* (2006.01)
*A61F 2/90* (2013.01)
*A61B 18/14* (2006.01)
*A61F 2/06* (2013.01)
*A61B 17/00* (2006.01)
*A61B 90/00* (2016.01)
*A61F 2/01* (2006.01)
*A61F 2/07* (2013.01)
*A61B 17/122* (2006.01)
*A61B 18/00* (2006.01)

(52) U.S. Cl.
CPC ............... *A61B 2017/00783* (2013.01); *A61B 2018/0022* (2013.01); *A61B 2018/00613* (2013.01); *A61B 2090/376* (2016.02); *A61B 2090/3966* (2016.02); *A61F 2/06* (2013.01); *A61F 2/07* (2013.01); *A61F 2002/016* (2013.01); *A61F 2250/0032* (2013.01); *A61F 2250/0098* (2013.01); *A61M 2025/09166* (2013.01)

(56) References Cited

U.S. PATENT DOCUMENTS

| | | | |
|---|---|---|---|
| 8,152,833 B2 | 4/2012 | Zaver et al. |
| 8,394,119 B2 | 3/2013 | Zaver et al. |
| 8,409,270 B2 | 4/2013 | Clerc et al. |
| 8,852,265 B2 | 10/2014 | Clerc et al. |
| 9,038,260 B2 | 5/2015 | Wu |
| 9,168,160 B2 | 10/2015 | Jensen et al. |
| 9,259,515 B2 | 2/2016 | Wang |
| 9,265,866 B2 | 2/2016 | Kramer-Brown et al. |
| 9,320,590 B2 | 4/2016 | Zaver et al. |
| 9,358,325 B2 | 6/2016 | Wu |
| 9,498,296 B2 | 11/2016 | Hingston et al. |
| 9,532,888 B2 | 1/2017 | Dugan et al. |
| 2003/0176884 A2 | 9/2003 | Berrada et al. |
| 2007/0208373 A1 | 9/2007 | Zaver et al. |
| 2008/0221670 A1* | 9/2008 | Clerc ...................... A61F 2/07 623/1.34 |

FOREIGN PATENT DOCUMENTS

EP 2990011 A1 3/2016
EP 3132770 A1 2/2017

\* cited by examiner

DEVICES AND METHODS OF USE WITH DEVICES HAVING A RADIOPAQUE FILAMENT

PRIORITY

This application claims the benefit of priority under 35 U.S.C. § 119 to U.S. Provisional Patent Application Ser. No. 62/509,379, filed May 22, 2017, which is incorporated by reference herein in its entirety and for all purposes.

FIELD

The present disclosure relates generally to medical devices and methods for medical devices to be placed within a lumen of a patient, wherein the devices comprise one or more radiopaque filaments arranged with the devices and viewable to assist in placement and orientation of the devices with respect to the lumen.

BACKGROUND

Medical devices developed for implantation or insertion into patients are known for various purposes including, as examples, stenting, drainage, or distal protection in and with respect to lumens, tracts, vessels, and cavities within the body. Implantable medical devices may be woven endoprostheses including stents, stent-grafts, or grafts used with percutaneous transluminal coronary angioplasty and in other medical procedures to repair and support diseased or damaged vessels and other body lumens.

Such medical devices may include expandable devices such as balloon catheters to dilate and treat body lumens to repair or remove lesions and promote lumen patency, either alone or in conjunction with other devices such as stents or stent-grafts.

In order to visualize the passage and placement of a medical device in body lumens, many procedures, including less invasive catheter-based procedures, are performed under fluoroscopy x-ray imaging, ultrasound, or some combination. The delivery device and/or medical device may be visualized with such modes of imaging if they are radiopaque and offer radiographic contrast relative to the body. For example, x-ray radiation may be used externally to visualize delivery devices and deployment of medical devices in the body. Also, radiographic contrast solution may be injected into the body lumen so that the lumen may be seen in the fluoroscopic image.

Physicians are challenged to precisely place medical devices at remote and specific intraluminal locations. Specifically, physicians are challenged with the position (orientation, deformity, etc.) of the device in its entirety or of particular sections or features of the device with respect to the location of placement and the purpose for which the devices are being placed.

SUMMARY

The devices and methods of the present disclosure, in their various aspects and embodiments, include a radiopaque filament arranged in the medical devices to provide improved visibility and positioning in order to address the challenges discussed above.

Embodiments of a medical device for placement within a lumen of a patient may include a body having a length and a longitudinal axis along the length. A device may include a first radiopaque filament having a length and at least one radiopaque portion along the length, the radiopaque portion including a radiopaque material and the first radiopaque filament outlining a first contour of the device. A device may include a second radiopaque filament having a length and being circumferentially offset from the first radiopaque filament about the longitudinal axis, the second radiopaque filament having at least one radiopaque portion along the length, the radiopaque portion including a radiopaque material and the second radiopaque filament outlining a second contour of the medical device.

A medical device may include a body comprising a plurality of filaments woven into a shape of the body of the medical device, the woven shape including a first contour and a second contour. Woven filaments may be woven in a pattern and a first and a second radiopaque filament may comprise filaments within the pattern. A first radiopaque filament may be disposed alongside one of a plurality of filaments. A shape of a body may be tubular, U-shaped, cylindrical, barbelled, oblong, circular, bent, concave within a cylindrical surface, convex within a cylindrical surface, or bulbous. A second radiopaque filament may be circumferentially offset from a first radiopaque filament by 90 degrees. A second radiopaque filament may be circumferentially offset from a first radiopaque filament by 180 degrees. A second radiopaque filament may be circumferentially offset from a first radiopaque filament by any number of degrees that is suitable for the intended purpose of positioning and/or orienting a device according to the offset. A body may include an expandable member and a first and a second radiopaque filament that are disposed about an outer surface of the expandable member. A first and a second radiopaque filament may be configured to expand and contract along with an outer surface of an expandable member.

A medical device may include a radiopaque portion of a first radiopaque filament that has a first radiopacity value, a radiopaque portion of a second radiopaque filament that has a second radiopacity value. The first radiopacity value may be different than the second radiopacity value. A lumen of a patient within which a medical device is placed may be a cavity, an organ, a vessel and a tract. A radiopaque material may be included on or in a radiopaque portion of a first and a second radiopaque filament by one or more of coating, impregnating, or cladding. A first and a second radiopaque filament may outline a respective first and second contour by extending along predetermined paths in a body of the medical device.

A medical device for placement within a lumen of a patient may include a body comprising a plurality of woven filaments, one or more of the plurality of woven filaments comprising a radiopaque portion that includes a radiopaque material. A plurality of filaments may be woven in a pattern and with a shape that defines a body. One or more filaments may have a radiopaque portion that outlines at least one contour of a shape of a body. A plurality of woven filaments may include a radiopaque portion that are at least two filaments that are offset from each other by 90 degrees circumferentially about a longitudinal axis of the medical device. A plurality of woven filaments may include a radiopaque portion that are at least two filaments that are offset from each other by 180 degrees circumferentially about a longitudinal axis of the medical device. A body may include an expandable member and a plurality of woven filaments with a radiopaque portion that are disposed about the expandable member. A plurality of woven filaments may include a radiopaque portion that are disposed alongside one or more woven filaments that do not comprise a radiopaque portion. A first and a second contour may correspond to a desired orientation of a medical device when placed in a patient lumen.

A method of delivering a medical device within a lumen of a patient may include positioning a medical device in a patient. A medical device may include at least one filament outlining a contour of the medical device, the filament having at least one radiopaque portion, and the radiopaque portion including a radiopaque material. A method may include using the at least one filament to position a medical device within a lumen. A method may include imaging a medical device using fluoroscopy. A method may include confirming a position of a medical device by identifying an orientation of at least one filament and a contour of the device in relation to a lumen. A device may include two contours. At least one filament may include a first filament that traces a first contour and a second filament that traces a second contour. A lumen of a patient may be selected from the group consisting of a cavity, an organ, a vessel and a tract.

BRIEF DESCRIPTION OF THE DRAWINGS

Non-limiting examples of the present disclosure are described by way of example with reference to the accompanying figures, which are schematic and not intended to be drawn to scale. In the figures, each identical or nearly identical component illustrated is typically represented by a single numeral. For purposes of clarity, not every component is labeled in every figure, nor is every component of each embodiment of the disclosure shown where illustration is not necessary to allow those of skill in the art to understand the disclosure. In the figures.

Figure 1A:
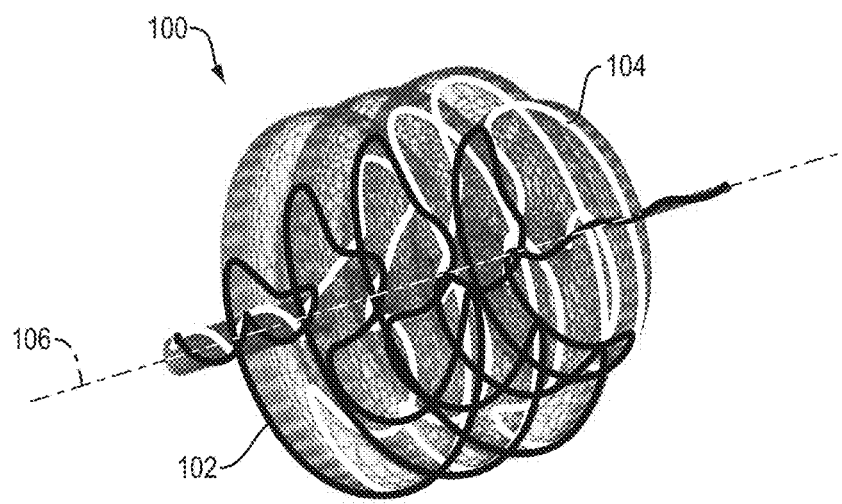
FIG. 1A is an isometric view of a medical device with two radiopaque filaments having a particular orientation with respect to each other, according to an embodiment of the present disclosure.

It is noted that the drawings are intended to depict only typical or exemplary embodiments of the disclosure. Accordingly, the drawings should not be considered as limiting the scope of the disclosure.

DETAILED DESCRIPTION

Various embodiments of devices, systems and methods in accordance with the present disclosure include medical devices positioned in a patient, and more particularly medical devices with one or more radiopaque filaments viewable using fluoroscopy, or x-ray imaging. The devices may be stents made up of multiple filaments woven throughout the device so as to define a lumen about a longitudinal axis of the stent. Additionally, or in the alternative, devices may include expandable member portions along a body of the device. In each case, the medical devices for placement within a lumen of a patient, e.g., cavity, vessel, organ, tract, comprising a body having a length and a longitudinal axis along the length. The medical devices comprise a first radiopaque filament having a length and at least one radiopaque portion along the length, the radiopaque portion including a radiopaque material and the first radiopaque filament outlining a first contour of the device. The medical device may have additional radiopaque filaments having a length and being circumferentially offset with respect to other radiopaque filaments about the longitudinal axis, the additional radiopaque filaments having at least one radiopaque portion along the length, the radiopaque portions including a radiopaque material and the additional radiopaque filament outlining additional contours of the medical devices.

In various embodiments described here or otherwise within the scope of the present disclosure, medical devices may have a plurality of filaments woven, or otherwise arranged, together to form the shape of the medical devices having one or more contours. Alternatively, the medical devices may be a balloon or other expandable member with filaments on an outer surface of the member. The filaments may comprise materials having shape memory effects and superelasticity such as, for example, a shape memory alloy such as nitinol or a shape memory polymer. These types of filaments have the ability to undergo deformation, such as being constrained, while a device is delivered into a patient, and later expanded once the device is positioned at a target delivery site and deployed. The filaments may be wires, coils, strands, or the like. The filaments may undergo deformation at one temperature and then recover their shape upon heating above a certain transformation temperature.

In various embodiments described here or otherwise within the scope of the present disclosure, a portion of, or all of, a length of the one or more of the filaments may be coated, plated, clad, or impregnated, with a radiopaque material. Different methods may be used to include radiopaque material among different filaments. Radiopaque, radiodensity, and radiopacity refer to the relative inability of electromagnetic radiation, particularly x-rays, to pass through a material. Suitable materials with high radiopacity for use with the filaments include tantalum, platinum, iridium, and tungsten, among others possible materials. Depending on the radiopacity of the portions of filaments within certain areas of devices, such areas may be separately identifiable through a fluoroscope. This may be accomplished within the same filament or among multiple filaments by using more than one radiopaque material along the length to identify or outline distinguishing portions (e.g., contours) of the devices. This may also be accomplished in the filaments through varying densities of the same radiopaque material.

In order for a medical device or portion of a device to be radiopaque, it must be made from a material possessing radiographic density higher than a surrounding host tissue and have sufficient thickness to affect the transmission of x-rays to produce contrast in the image. A medical device may be made of metals including tantalum or platinum having relatively high radiographic densities. Other metals such as stainless steel, superalloys, nitinol, and titanium having lower radiographic densities may also be used. Examples of medical devices with details of how radiopacity may be achieved include U.S. Pat. Nos. 4,447,239; 4,655,771; 4,954,126; 5,061,275; 5,354,257; 5,423,849; 5,630,840; and 6,340,367, the entire disclosures of which are incorporated herein by reference in their entirety.

Polymeric medical devices are generally radiolucent and do not possess sufficient radiographic density to be easily imaged by fluoroscopy. To improve the imaging of polymeric materials, polymers may be mixed with radiopaque filler materials prior to molding or extruding in order to enhance the radiographic density. However, a disadvantage of using fillers with polymers is that changes in the properties of the polymer may occur. For example, the addition of fillers may reduce the strength or ductility of the polymer. This effect may also be seen to some degree by adding fillers to metal filaments used to construct medical devices.

In the present disclosure, radiopaque filaments may be incorporated into or with medical devices without effecting or with minimal impact to the structural integrity or strength of the devices. Embodiments of devices with a radiopaque filament according to the present disclosure include at least one filament outlining a contour of the device. Radiopaque filaments may be woven throughout the devices. The radiopaque filament may be formed in unique shapes about the device, coincide with other filaments in a pattern, or be disposed/woven alongside another filament(s). When woven throughout the device, the radiopaque filaments may represent the position, shape, and/or deformation of the device generally. When the radiopaque filaments coincide with other filaments in a pattern, the radiopaque filaments may contribute to the structural integrity of the device as much as other filaments or not contribute to the structural integrity at all. Structural integrity may be accomplished by, for example, thickening of the radiopaque filaments or mixing or coating the radiopaque material with other materials. The radiopaque filaments may also take on their own unique path throughout the device, not coinciding or traveling along a similar or parallel path of any other filament.

In various embodiments described here or otherwise within the scope of the present disclosure, a radiopaque filament may not by woven throughout a device and may instead be structured only about a portion of a device. The portion of the device may be a notable feature or section of the device such as, for example, an electrode, a filter, an occlusive body, or an expandable portion or expandable member of the device, such as a balloon. Radiopaque filaments structured about a portion of a device may indicate the position, shape, and/or deformation of that portion and/or notable feature of the device. For example, radiopaque filaments structured about an expandable member of a device could be used to position and/or orient the device, or indicate an amount of expansion or contraction of the expandable member.

Embodiments of devices according to the present disclosure may include more than one filament with radiopaque portions. A device with two (or more) radiopaque filaments may have a second radiopaque filament extending along a different path than a first radiopaque filament. The second path may outline a second contour of the device, different than a first contour outlined by the first radiopaque filament, each viewable through imaging using a fluoroscope. Radiopaque filaments may be made discernable from each other by incorporating differences in their shape, position, and/or radiopacity. Multiple radiopaque filaments outlining separate contours of the device may better define the shape and position of the device within a patient using fluoroscope imagery. The contours may represent certain sections or features of the device for proper positioning and orientation by a medical professional with respect to a particular location and/or desired function. Multiple contours of the device may be outlined by radiopaque filaments such that they define all or most of a device's desired deformation, shape, and/or position within a patient. For example, a portion of a device may be undesirably compressed against a tissue of a patient and may need to be repositioned. For another example, a device may be oriented in an undesirable direction and may need to be repositioned in order to function as desired. For another example, a device may be located at an undesirable site within a patient and may need to be moved to another desirable site for treatment.

Embodiments of devices according to the present disclosure may include a body comprising a plurality of filaments woven into a shape of the body of the medical device. The woven shape may include one or more contours. The shape of the body of the device may take on numerous shapes such as, e.g., tubular, U-shaped, cylindrical, barbelled, oblong, circular, bent, or bulbous. These devices may be positioned within a lumen of a patient. A lumen may be, e.g., a cavity, an organ, a vessel or a tract.

Referring to FIGS. 1A through 1D, an embodiment of a device with two radiopaque filaments according to the present disclosure includes a body 100 with a length and a longitudinal axis 106 along the length. The device is a stent for closure of the left atrial appendage. The device may be collapsed and delivered into the left atrial appendage via a catheter. The device is drawn into the catheter along its longitudinal axis and then placed (pushed out) into the left atrial appendage cavity. In FIG. 1A, a first radiopaque filament 102 extends along a path of the body 100. The radiopaque filament 102 outlines a contour that is part of a woven pattern of filaments of the body 100. A second radiopaque filament 104 extends along another path of the body 100, outlining a second contour that is part of the woven pattern of filaments.

Figure 1B:
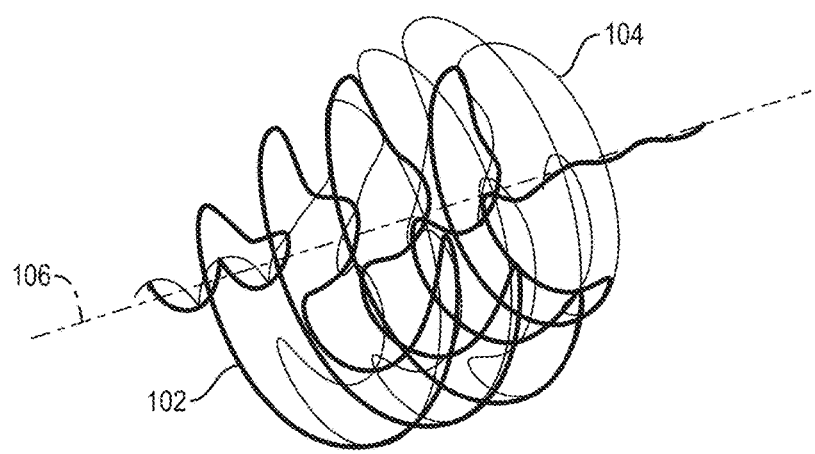
FIG. 1B is an isometric view of the medical device of FIG. 1A using fluoroscopic imaging.

FIG. 1B illustrates the path of the first radiopaque filament 102 and the second radiopaque filament 104 of the device of FIG. 1A and the outline of each when in the body 100, as viewed using fluoroscopy. The first radiopaque filament 102 has a radiopacity value that is different than the radiopacity value of the second radiopaque filament 104. This helps the user to separately identify the first radiopaque filament 102 from the second radiopaque filament 104. The second filament 104 is circumferentially offset from the first filament 102 about the longitudinal axis 106. In other embodiments the radiopacity values may be the same, or some may be the same and the values of other radiopaque filaments may vary.

Figure 1C:
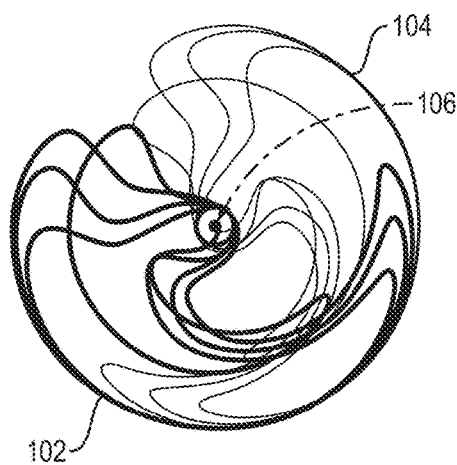
FIG. 1C is a front view of the medical device of FIGS. 1A-1B using fluoroscopic imaging.

FIG. 1C illustrates the first radiopaque filament 102 and second radiopaque filament 104 of FIGS. 1A and 1B when viewed by fluoroscopic imaging from the front. The viewpoint illustrates the orientation of the filaments and amount of radial deformation of the device due to compression by the body lumen walls. The second radiopaque filament 104 is circumferentially offset from the first radiopaque filament 102 by 90 degrees about the longitudinal axis.

While an offset of 90 degrees is illustrated in FIGS. 1A-1C, in this and any other embodiments, any amount of offset between the first filament 102 and the second filament 104 about the longitudinal axis 106 may be selected, such as, for example, 45 degrees, 60 degrees, 180 degrees, 270 degrees, etc. Any degree of offset selected may be based on the specific device configuration and the intended needs of the medical procedure of which it is involved. Various positions of the first filament 102 and second filament 104 may be selected to outline contours of the body 100 that correlate to notable sections or features of the device. For example, the image of the device provided by the filaments show that the device is positioned in an undesirable orientation, the device may be rotated about the longitudinal axis 106 in order to attain a desired orientation. For example, the first filament 102 is generally positioned in the lower left region of FIG. 1C, while the second filament is generally positioned in the upper right region of FIG. 1C. Rotating the body 100 about the longitudinal axis 106 may change how the first filament 102 and second filament 104 are oriented within a patient.

Figure 1D:
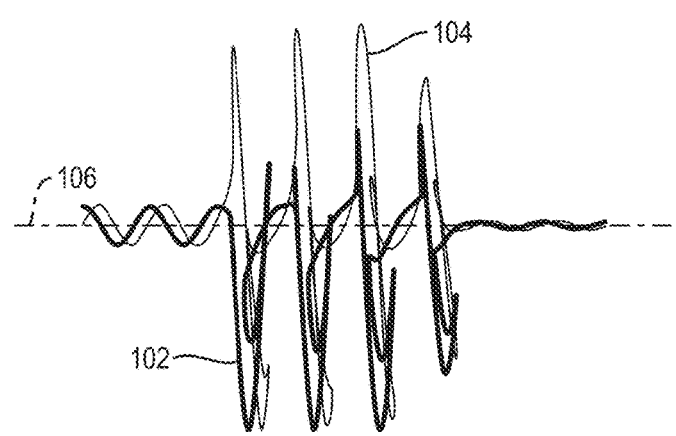
FIG. 1D is a right view of the medical device of FIGS. 1A-1C using fluoroscopic imaging.

FIG. 1D illustrates the first radiopaque filament 102 and second radiopaque filament 104 of FIGS. 1A through 1C when viewed by fluoroscopic imaging from the right. The right viewpoint illustrates the distal and proximal location of the medical device within a patient body lumen, deformation of the device due to compression by body lumen walls, and axial compression of the device along the longitudinal axis 106. Should the device be positioned in an undesirable location or undesirably deformed when fluoroscopically inspected, the device may be reoriented or repositioned within the patient. Through further fluoroscopic inspection of the first radiopaque filament 102 and second radiopaque filament 104, the device can be confirmed to be in a desirable location and/or desirable deformation.

Figure 2A:
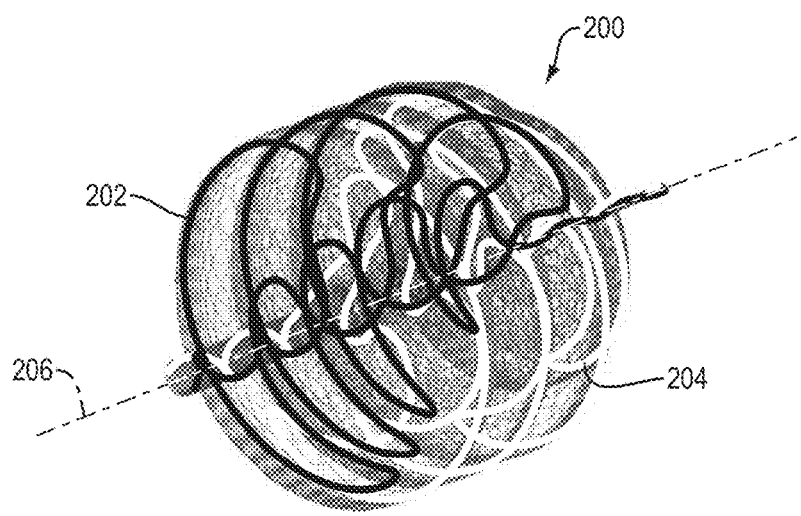
FIG. 2A is an isometric view of a medical device with two radiopaque filaments having a particular orientation with respect to each other, according to an embodiment of the present disclosure.

Referring to FIGS. 2A through 2D, an embodiment of a device with a radiopaque filament according to the present disclosure includes a body 200 with a length and a longitudinal axis 206 along the length. The device is a stent for closure of the left atrial appendage. The device may be collapsed and delivered into the left atrial appendage via a catheter. The device is drawn into the catheter along its longitudinal axis and then placed (pushed out) into the left atrial appendage cavity. In FIG. 2A, a first radiopaque filament 202 extends along a path of the body 200. The radiopaque filament 202 outlines a contour of the shape of the body that is part of a woven pattern of filaments of the body 200. A second radiopaque filament 204 extends along another path of the body 200, outlining a second contour of the shape of the body that is part of the woven pattern of filaments.

Figure 2B:
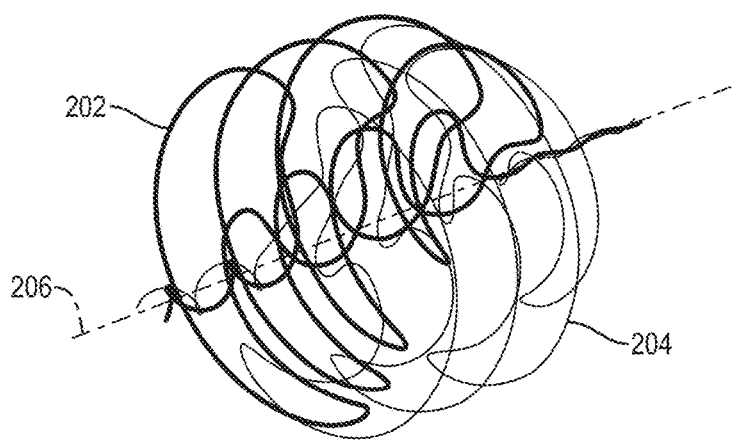
FIG. 2B is an isometric view of the medical device of FIG. 2A using fluoroscopic imaging.

FIG. 2B illustrates the path of the first radiopaque filament 202 and the second radiopaque filament 204 of the device in FIG. 2A and the outline of each when in the body 200, as viewed using fluoroscopy. The first radiopaque filament 202 has a radiopacity value that is different than the radiopacity value of the second radiopaque filament 204. This helps the user to separately identify the first radiopaque filament 202 from the second radiopaque filament 204. The second filament 204 is circumferentially offset from the first filament 202 about the longitudinal axis 206. In other embodiments the radiopacity values may be the same, or some may be the same and some values of other radiopaque filaments may vary.

Figure 2C:
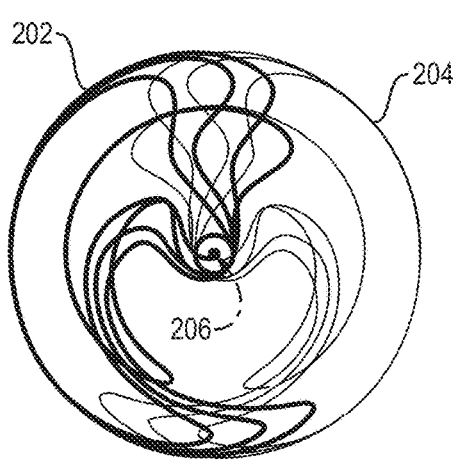
FIG. 2C is a front view of the medical device of FIGS. 2A-2B using fluoroscopic imaging.

FIG. 2C illustrates the first radiopaque filament 202 and second radiopaque filament 204 of FIGS. 2A and 2B when viewed by fluoroscopic imaging from the front. The viewpoint illustrates the orientation of the filaments and radial deformation of the filaments due to the walls of the bodily lumen. Filament 204 is offset from the first filament 202 by 180 degrees about the longitudinal axis.

While an offset of 180 degrees is illustrated in FIGS. 2A-2C, in this and any other embodiments, any amount of offset between the first filament 202 and the second filament 204 about the longitudinal axis 206 may be selected, such as, for example, 45 degrees, 60 degrees, 90 degrees, 270 degrees, etc.

Various positions of the first filament 202 and second filament 204 may be selected to outline contours of the body 200 that correlate to notable sections or features of the device. FIG. 2C illustrates that an entire circumference and contour of the body 200 may be outlined by the combined first paths of the first radiopaque filament 202 and the second radiopaque filament 204. This orientation of radiopaque filaments is different than that of FIG. 1C where a portion of the circumference of the body 100 does not include a radiopaque filament when viewed from the front view. The 180 degree offset in FIG. 2C of the radiopaque filaments may show deformation in any portion of the outline of the device created by the combined radiopaque filaments. The circumference may be the inner circumference, outer circumference, or a circumference in between the body 200. The outline of the circumference created by the radiopaque filaments in this view may transition at certain portions along the lengths of the radiopaque filaments from an outer circumference to an inner circumference of the body 200. For example, the image of the device provided by the filaments show that the device is positioned in an undesirable orientation, the device may be rotated about the longitudinal axis 206 in order to attain a desired orientation. For example, the first filament 202 is generally positioned in the left region of FIG. 2C while the second filament is generally positioned in the right region of FIG. 2C. Rotating the body 200 about the longitudinal axis 206 may change how the first filament 202 and second filament 204 are oriented within a patient.

Figure 2D:
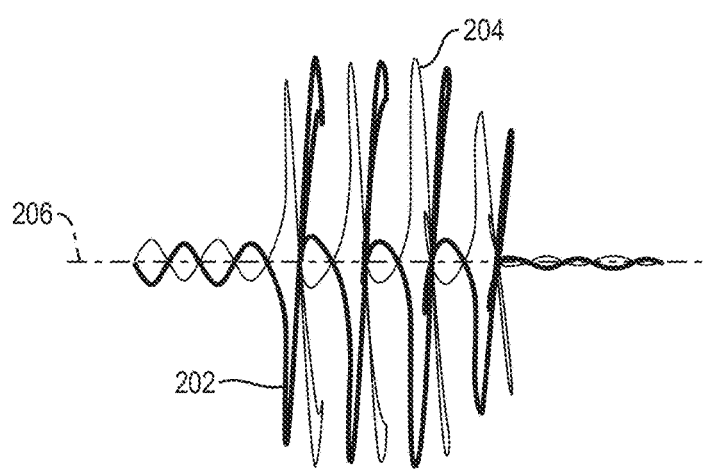
FIG. 2D is a right view of the medical device of FIGS. 2A-2C using fluoroscopic imaging.

FIG. 2D illustrates the first radiopaque filament 202 and the second radiopaque filament 204 of FIGS. 2A through 2C when viewed by fluoroscopic imaging from the right. The right viewpoint illustrates the distal and proximal location of the medical device within a patient body lumen, deformation of the device due to compression by body lumen walls, and axial compression of the device along the longitudinal axis 206. Should the image of the device provided by the filaments show that the device is positioned in an undesirable location or undesirably deformed when fluoroscopically inspected, the device may be reoriented within the patient in order to attain a desired orientation. Through further fluoroscopic inspection of the first radiopaque filament 202 and second radiopaque filament 204, the device can be confirmed to be in a desirable location with desirable deformation.

Figure 3:
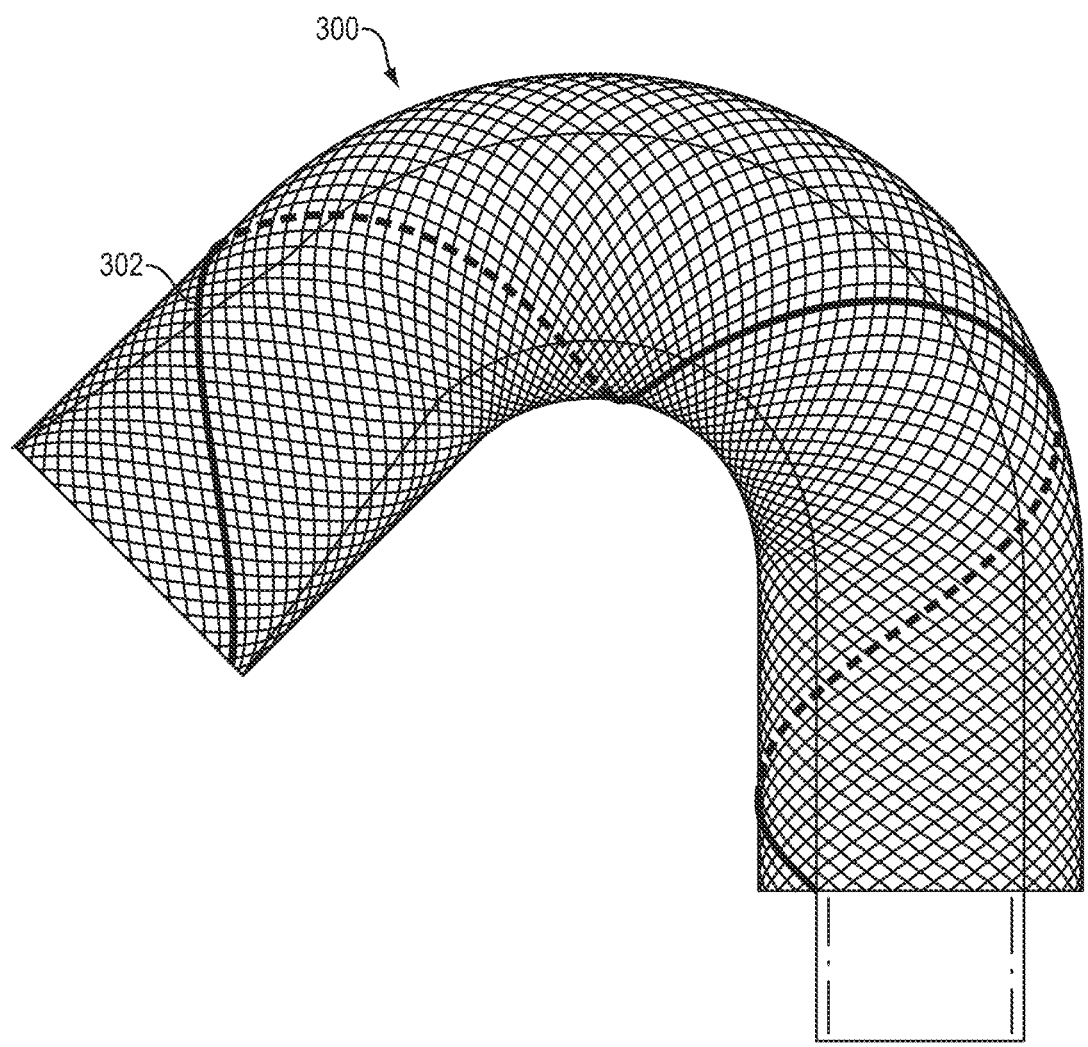
FIG. 3 is a top view of a medical device with one radiopaque filament, according to an embodiment of the present disclosure.

FIG. 3 depicts an exemplary device that is an embodiment of an aortic arch filtration device. Variations on these devices and other devices, and associated components and features which may be suitable for the devices of the present disclosure, can be found in U.S. application Ser. No. 14/049,385, the entire disclosure of which is incorporated by reference herein in its entirety. The device is used for preventing emboli and other debris from entering the carotid arteries (i.e., the right common carotid artery and/or the brachiocephalic artery, and the left common carotid artery) to reduce the incidence of ischemic stroke. The device may be delivered over a catheter and disposed between the brachiocephalic artery and the left subclavian artery. It may be oriented in a wide U-shape at this location.

The device in FIG. 3 includes a body 300 with a length. The body 300 may be made up of woven filaments that may form a pattern. The pattern may be a helical pattern and it may form a lumen throughout the body. Within the lumen is a polymer-based tubular body filter for embolic protection in the aortic arch. A radiopaque filament 302 outlines a contour that is part of the woven pattern of filaments of the body 300. The body 300 in FIG. 3 is formed into a bend, which deforms the radiopaque filament 302. Through fluoroscopic imaging, formation of the radiopaque filament 302, and therefore the deformation of the device, may be observable for proper placement of the device.

FIGS. 4A through 4D depict a device that is an embodiment of a mitral/tricuspid annular reduction anchor device. Variations on these devices and other devices, and associated components and features which may be suitable for the devices of the present disclosure, can be found in U.S. application Ser. Nos. 13/242,953, 13/241/603, and 14/950,637, the entire disclosures of which are incorporated by reference herein in their entirety. The device is used to assist with the necrosis and otherwise weakening, thinning of, and widening of the walls of heart valves. The device may be oriented surrounding and/or in place of heart valves and/or walls.

The device in FIG. 4 depicts an exemplary embodiment of a device with a radiopaque filament including a body 400 with a length and a longitudinal axis 406 along the length. In FIG. 4A, a first radiopaque filament 402 extends along a path of the body 400. The radiopaque filament 402 outlines a contour that is part of a woven pattern of filaments of the body 400. A second radiopaque filament 404 extends along another path of the body 400, outlining a second contour that is part of the woven pattern of filaments.

Figure 4A:
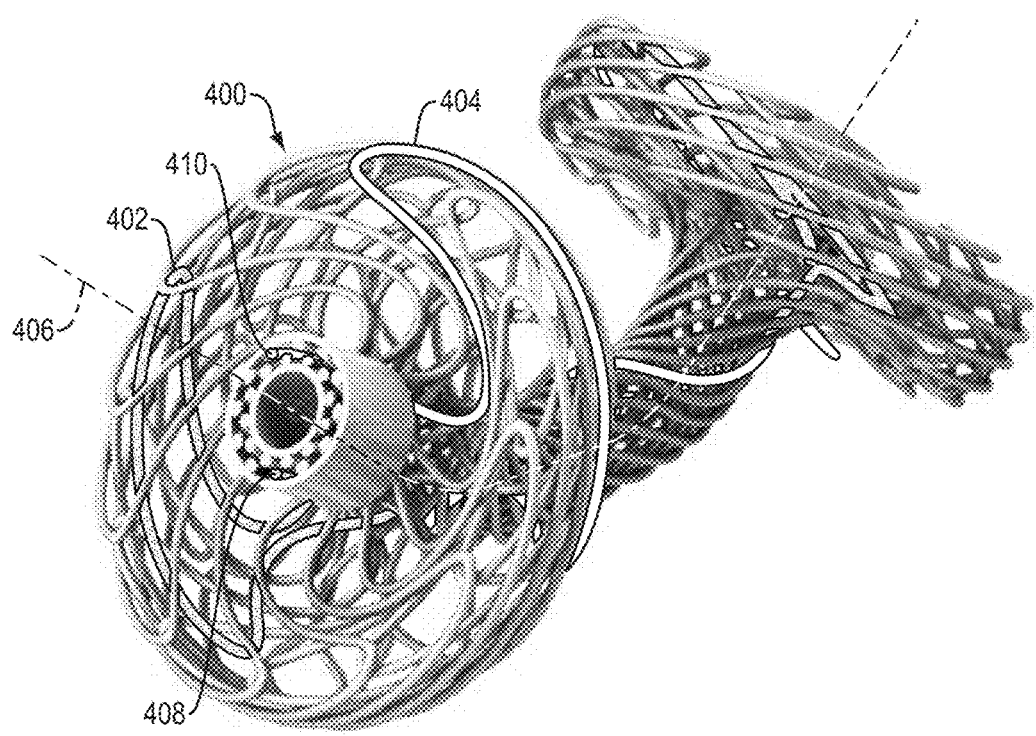
FIG. 4A is an isometric view of a medical device with two radiopaque filaments having a particular orientation with respect to each other, according to an embodiment of the present disclosure.
Figure 4B:
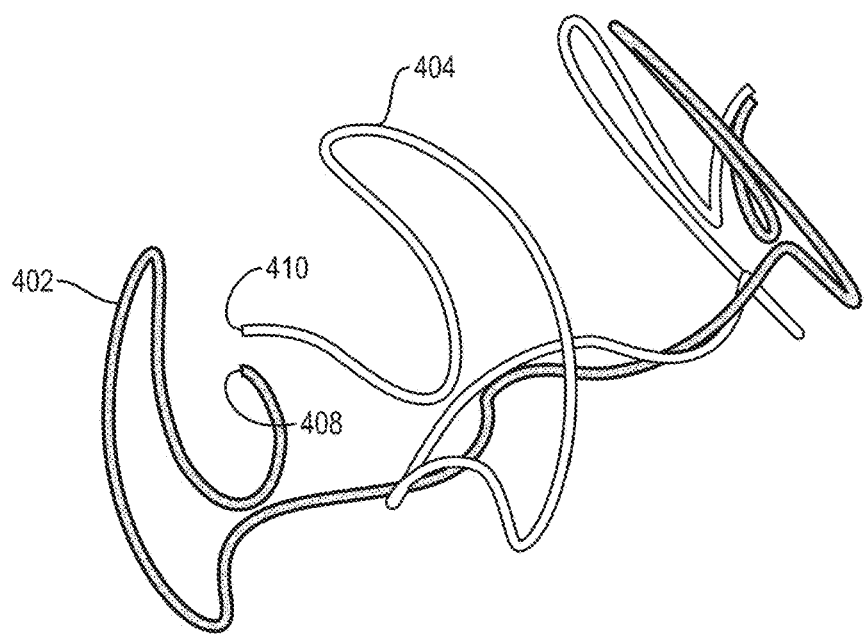
FIG. 4B is an isometric view of the medical device of FIG. 4A using fluoroscopic imaging.

FIG. 4B illustrates the path of the first radiopaque filament 402 and the second radiopaque filament 404 of the device of FIG. 4A and the outline of each when in the body 400, as viewed using fluoroscopy. The first radiopaque filament 402 has a radiopacity value that is different than the radiopacity value of the second radiopaque filament 404. This helps the user to separately identify the first radiopaque filament 402 from the second radiopaque filament 404. The second radiopaque filament 404 is circumferentially offset from the first radiopaque filament 402 about the longitudinal axis 406. In other embodiments the radiopacity values may be the same, or some may be the same and the values of other radiopaque filaments may vary. Filament 404 is offset from the first filament 402 by 180 degrees about the longitudinal axis. This is illustrated in FIG. 4A where an end 408 of the first radiopaque filament 402 is offset 180 degrees from an end 410 of the second radiopaque filament 404 about the longitudinal axis 406. While an offset of 180 degrees is illustrated in these figures, any amount of offset between the first filament 402 and the second filament 404 about the longitudinal axis 406 may be selected, such as, for example, 45 degrees, 60 degrees, 90 degrees, 270 degrees, etc.

Figure 4C:
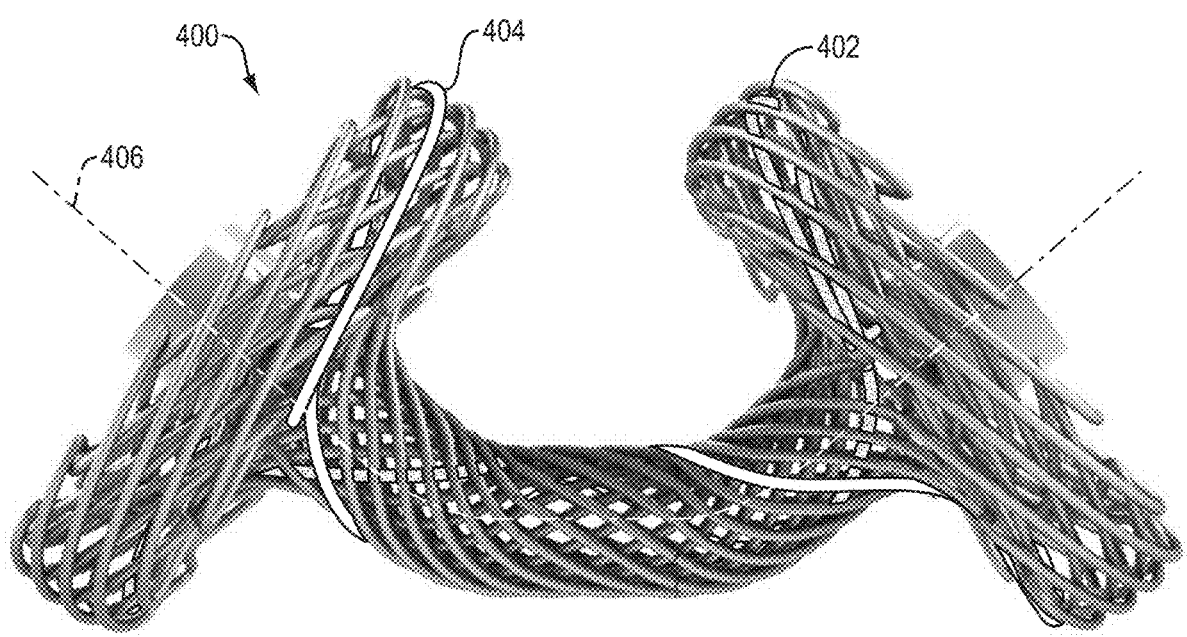
FIG. 4C is a right view of the medical device of FIG. 4A.
Figure 4D:
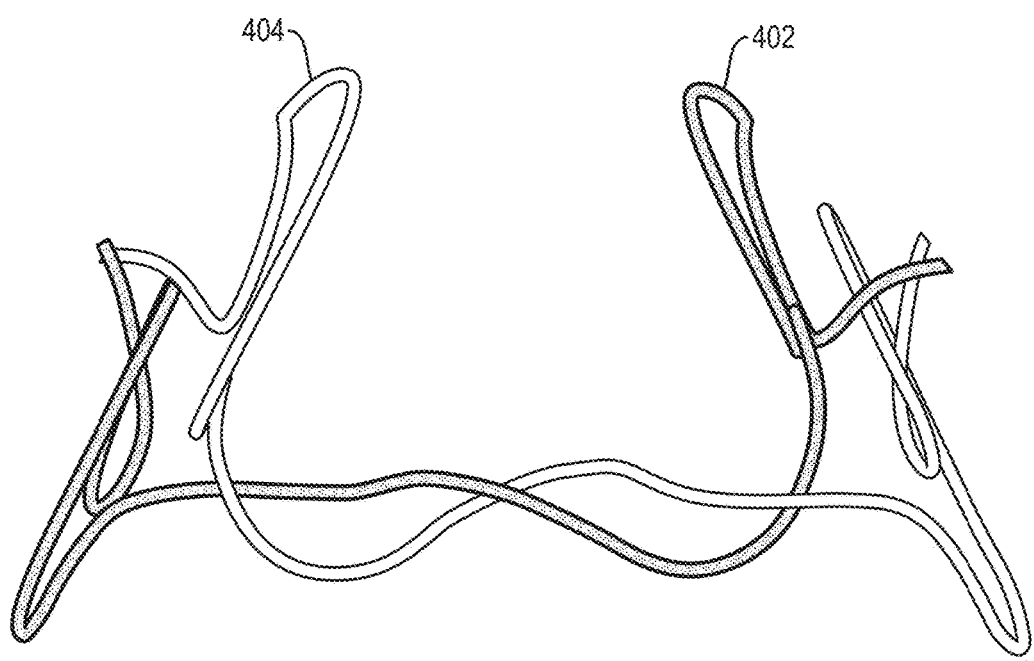
FIG. 4D is a right view of the medical device and radiopaque filaments of FIGS. 4A through 4C using fluoroscopic imaging.

FIG. 4C illustrates a body 400 and radiopaque filaments 402 and 404 of FIGS. 4A and 4B from the right view, while FIG. 4D illustrates the first radiopaque filament 402 and second radiopaque filament 404 of FIGS. 4A through 4C when viewed by fluoroscopic imaging from the right. The right viewpoint illustrates the distal and proximal location of the medical device within a patient body lumen, deformation of the device due to compression by body lumen walls, and axial compression of the device along the longitudinal axis 406. Should the image of the device provided by the filaments show that the device is positioned in an undesirable orientation or undesirably deformed when fluoroscopically inspected, the device may be reoriented within the patient in order to attain a desired orientation. Through further fluoroscopic inspection of the first radiopaque filament 402 and second radiopaque filament 404, the device can be confirmed to be in a desirable orientation with desirable deformation.

Figure 5A:
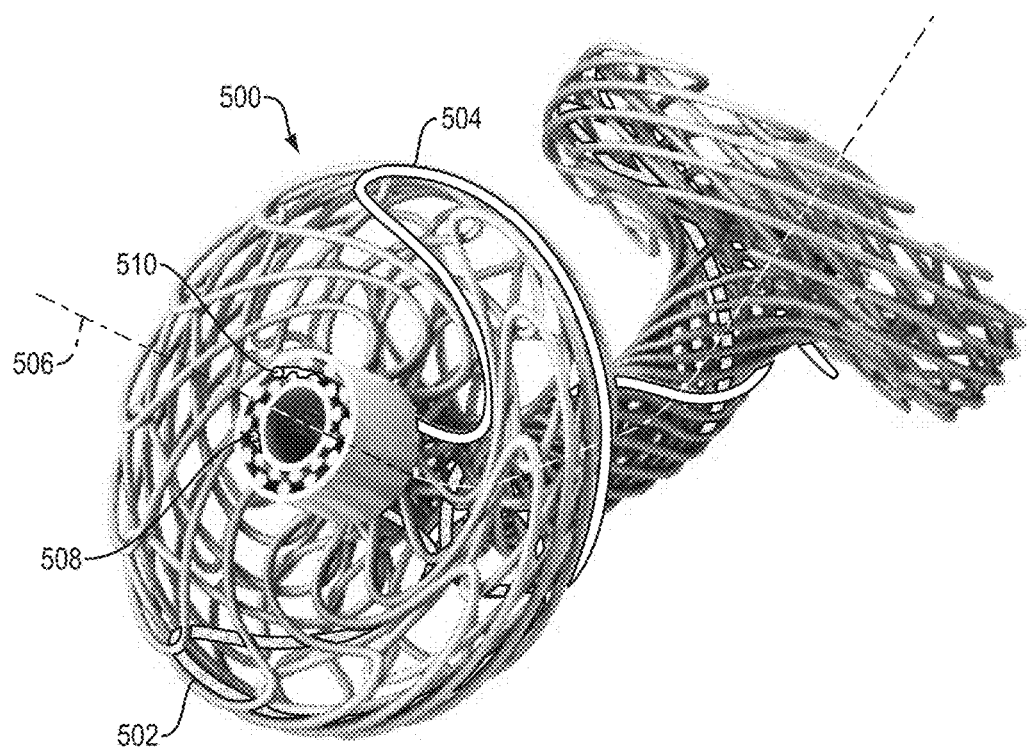
FIG. 5A is an isometric view of a medical device with two radiopaque filaments having a particular orientation with respect to each other, according to an embodiment of the present disclosure.
Figure 5B:
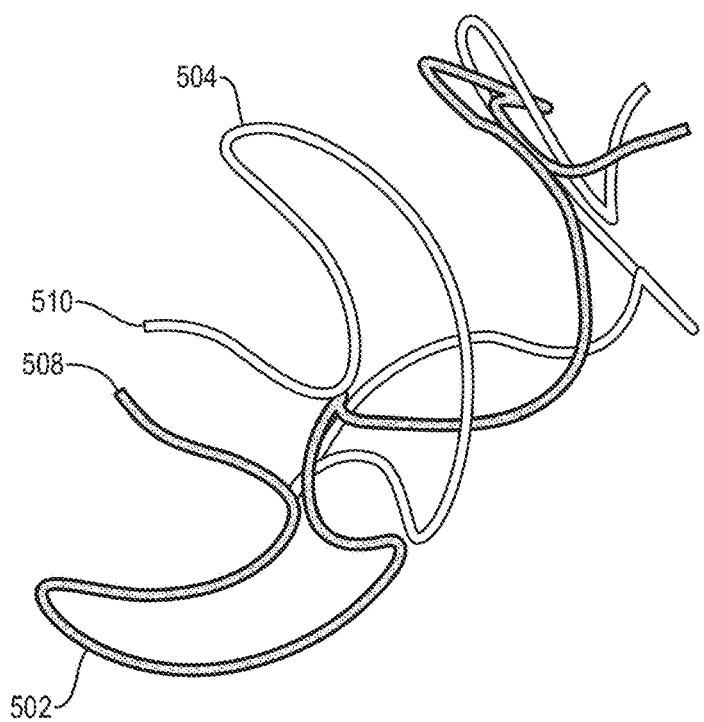
FIG. 5B is an isometric view of the medical device of FIG. 5A using fluoroscopic imaging.

FIGS. 5A and 5B depict an exemplary device with a radiopaque filament according to the present disclosure includes a body 500 with a length and a longitudinal axis 506 along the length. The device illustrated here is a mitral/tricuspid annular reduction anchor device.

FIG. 5A illustrates the path of a first radiopaque filament 502 extending along a path and outlining a contour of the body 500. The first radiopaque filament 502 outlines a contour that is part of a woven pattern of filaments of the body 500. A second radiopaque filament 504 extends along another path of the body 500, outlining a second contour that is part of the woven pattern of filaments. FIG. 5B illustrates the first radiopaque filament 502 and the second radiopaque filament 504 of the device without the body 500, as viewed using fluoroscopy. The first radiopaque filament 502 has a radiopacity value that is different than the radiopacity value of the second radiopaque filament 504. This helps the user to separately identify the first radiopaque filament 502 from the second radiopaque filament 504. The second radiopaque filament 504 including end 510 is circumferentially offset from the first radiopaque filament 502 including end 508 about the longitudinal axis 506. In other embodiments the radiopacity values may be the same, or some may be the same and the values of other radiopaque filaments may vary. While an offset of 90 degrees is illustrated in these figures, any amount of offset between the first radiopaque filament 502 and the second radiopaque filament 504 about the longitudinal axis 506 may be selected, such as, for example, 45 degrees, 60 degrees, 180 degrees, 270 degrees, etc.

Figure 6A:
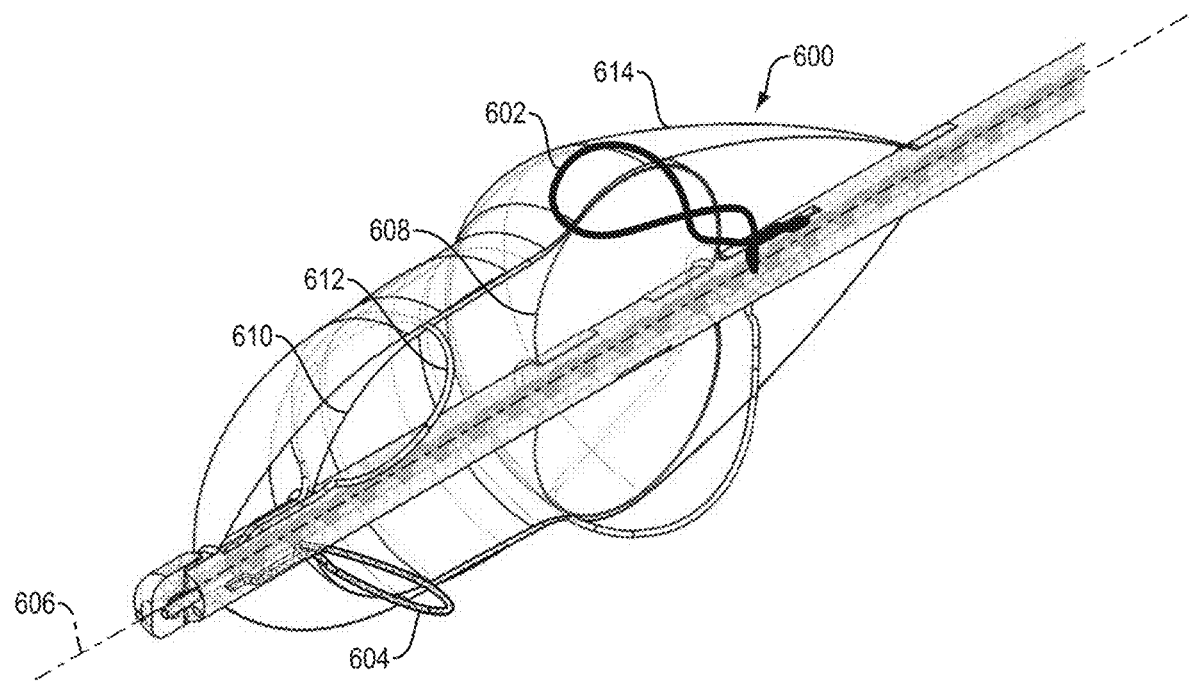
FIG. 6A is an isometric cross-sectional view of a medical device according to an embodiment of the present disclosure.
Figure 6B:
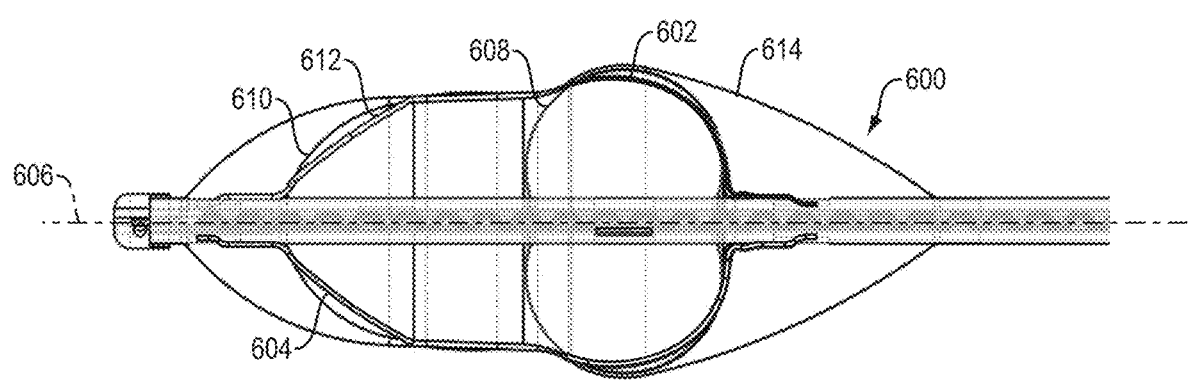
FIG. 6B is a right view of the medical device of FIG. 6A.
Figure 6C:
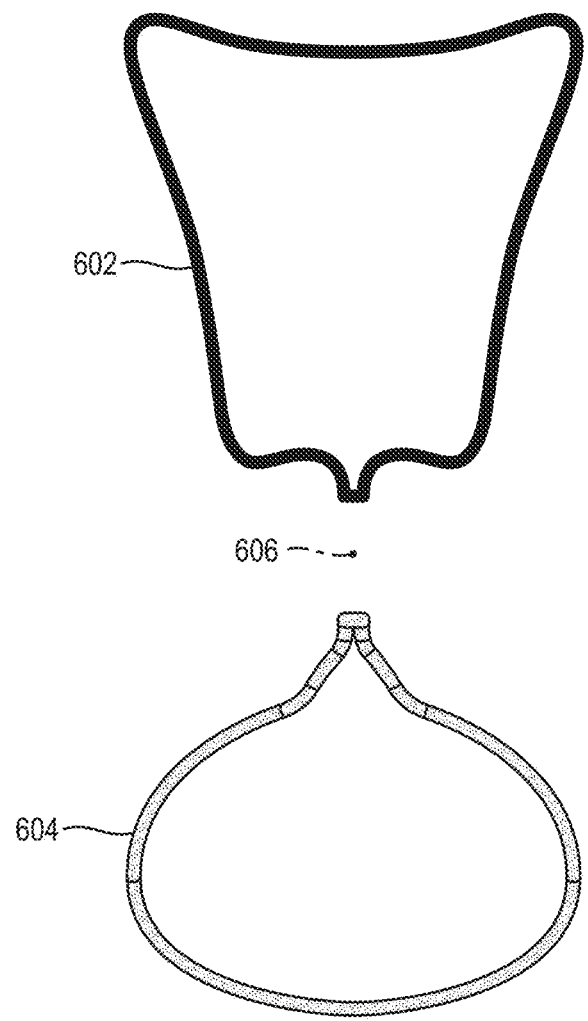
FIG. 6C is a front view of the medical device of FIGS. 6A and 6B using fluoroscopic imaging.

FIGS. 6A through 6C depict an exemplary device that is an embodiment of an irreversible electroporation (IRE) balloon device. The device delivers IRE therapy within the bodily lumens such as the pulmonary vein. In delivering the therapy, the device is positioned substantially axially within the bodily lumen that it is treating. Variations on these devices and other devices, and associated components and features which may be suitable for the devices of the present disclosure, can be found in U.S. application Ser. No. 15/290,580, the entire disclosure of which is incorporated by reference herein in its entirety.

FIG. 6A illustrates an embodiment of a device including a radiopaque filament according to the present disclosure. The device includes a body 600 with a length and a longitudinal axis 606 along the length. The isometric cross-sectional view is an expandable occlusion device including balloons 608, 610, and 614 that inflate with saline. The body 600 may include a porous section that allows a regulated flow of saline out of the device. The device includes four looped electrode wires 612. A patient may be treated with IRE therapy through a series of high voltage (e.g., about 1500 Vdc, or about 2000 Vdc, or any other voltage between 1,000-3,000 Vdc, depending on the application) pulses of a short duration (e.g., about 1-100 micro-seconds) from the electrode wires 612. The affected tissue is local to the area of the saline flow from the balloon. The therapy may result in pores in cellular walls of the patient to open, "void", and ultimately die. The device may act as a seal in, for example, the pulmonary vein. The saline may be a conduit path between the looped electrode wires 612 and target tissue.

FIG. 6A illustrates a first radiopaque filament 602 that outlines a contour that is one of the electrode wires 612 of the device. A second radiopaque filament 604 outlines a contour that is another one of the electrode wires 612. The radiopaque filaments are on opposite distal and proximal portions of the longitudinal axis 606. The radiopaque filaments are also circumferentially offset from each other about the longitudinal axis 606. While an offset of 180 degrees is illustrated in these figures, any amount of offset between the first filament 602 and the second filament 604 about the longitudinal axis 606 may be selected, such as, for example, 45 degrees, 60 degrees, 90 degrees, 270 degrees, etc. When the device is viewed through a fluoroscope, the position and orientation of the radiopaque filaments 602 and 604 and therefore the electrode wires 612 are viewable. Should the electrode wires 612 be in an undesirable location, they may be repositioned and/or reoriented. Since the electrode wires 612 are disposed about a surface of the expandable balloons 608 and 610 and inside of balloon 614, the electrode wires 612 may deform along with the expansion and contraction of the balloons 608 and 610. In this way, fluoroscopic imaging of the device reveals the first radiopaque filament 602 that coincides with the expansion and contraction of the balloon 608 while the second radiopaque filament 604 coincides with the expansion and contraction of the other balloon 610. FIG. 6B is an illustration of the device of FIG. 6A from a right viewpoint. The right view provides an angle of the embodiment to investigate the inflation/deflation states of balloons 608 and 610 via fluoroscopic imaging of the radiopaque filaments 602 and 604. FIG. 6C illustrates the device of FIGS. 6A and 6B from a front viewpoint as imaged via fluoroscopy. The front view illustrates how the second radiopaque filament 604 is circumferentially offset from the first radiopaque filament 602 by 180 degrees about the longitudinal axis 606.

Various embodiments of methods of use of the devices described here and other devices within the present disclosure, include delivering a device within a lumen of a patient, positioning a device in a patient with at least one filament outlining a contour of the medical device, the filament having at least one radiopaque portion, the radiopaque portion including a radiopaque material. The user may use at least one filament to position the medical device within the lumen. The user may image the device using fluoroscopy. The user may confirm a position of the medical device by identifying an orientation of the at least one filament and the contour of the device in relation to the lumen. At least one contour may comprise two contours and at least one filament may comprise a first filament that traces the first contour and a second filament that traces the second contour. The lumen may be a cavity, an organ, a vessel or a tract.

In variations of the embodiments described here or otherwise within the scope of the present disclosure, the materials of the filaments may be polymeric. Polymeric materials suitable for embodiments of the devices may comprise any polymer or polymer blend suitable for use in implantable or insertable medical devices. Polymers may be selected, for example, from suitable members of the following, among others: polyolefins such as polyethylenes (e.g., metallocene catalyzed polyethylenes), polypropylenes and polybutylenes; polyolefin copolymers, e.g., ethylenic copolymers such as ethylene vinyl acetate (EVA) copolymers, ethylene-methacrylic acid copolymers and ethylene-acrylic acid copolymers, where some of the acid groups can be neutralized with either zinc or sodium ions (commonly known as ionomers); vinyl aromatic polymers such as polystyrene; vinyl aromatic copolymers such as copolymers of olefins and styrene or alpha-methyl styrene, for example, butadiene-styrene copolymers and copolymers of polyisobutylene with polystyrene or polymethylstyrene, for example, polystyrene-polyisobutylene-polystyrene triblock copolymers; polyacetals; chloropolymers such as polyvinyl chloride (PVC); fluoropolymers such as polytetrafluoroethylene (PTFE); polyesters such as polyethyleneterephthalate (PET); polyester-ethers; polyamides such as nylon 6 and nylon 6,6; polyethers; polyamide ethers such as polyether block amides (PEBA) comprising (a) nylon blocks, for example, nylon 6, nylon 4/6, nylon 6/6, nylon 6/10, nylon 6/12, nylon 11 or nylon 12 blocks and (b) polyether blocks, for example, poly(ethylene oxide), poly(trimethylene oxide), poly(propylene oxide) or poly(tetramethylene oxide) blocks, one specific example of which is a poly(tetramethylene oxide)-b-polyamide-12 block copolymer, available from Elf Atochem as PEBAX; polyoctenamers such as Vestenamer® from Degussa Corp., Parsippany, N.J., which is a mixture of cyclic and linear polyoctenamers; elastomeric and thermoplastic polyurethanes, including polyurethane copolymers (including block and random copolymers that are polyether based, polyester based, polycarbonate based, aliphatic based, aromatic based and mixtures thereof), commercially available examples of which include Carbothane®, Tecoflex®, Tecothane®, Tecophilic®, Tecoplast®, Pellethane®, Chronothane® and Chronoflex®); and vinyl aromatic polymers and copolymers; silicones; polycarbonates; as well as mixtures of any of the foregoing, among others. The filaments may be made up of multiple layers of material for their properties (such as anti-encrustation, radiopacity, etc.). The filaments may be made up of differing materials from each other.

In variations of the embodiments described here or otherwise within the scope of the present disclosure, the filaments may also contain one or more optional additives, for example, selected from therapeutic agents, radiopaque agents, colorants, other optional additives such as plasticizers and extrusion lubricants, and combinations of the above, among others, in amounts effective to serve their intended purposes. Where used in the devices of the present disclosure, such optional additives may be present, for example, in the polymeric and metallic materials such as those discussed above, among others, or in coatings applied to the polymeric materials, or both.

Radiopaque agents facilitate viewing of the medical device during insertion of the device and at any point while the device is implanted. Radiopaque agents that may be useful for radiopaque filaments used in medical devices of the present disclosure, include bismuth salts such as bismuth subcarbonate, bismuth oxychloride, bismuth trioxide, barium sulfate, tungsten, and mixtures thereof. More specific examples of such radio-opaque agents include tungsten, platinum, tantalum, iridium, gold, or other dense metal, barium sulfate, bismuth subcarbonate, bismuth trioxide, bismuth oxychloride, metrizamide, iopamidol, iothalamate sodium, iodomide sodium, and meglumine, among others. A radiopaque agent is typically present in an amount of from about 10% to about 40% (including 10% to 15% to 20% to 25% to 30% to 35% to 40%, with 15-30% being more typical).

Additionally or alternatively, the polymeric material or additive material choice, as well as extrusion technique, may be optimized to enhance device contrast using ultrasound imaging. The incorporation of sonographic agents, in addition to or as an alternative to radiopaque agents, such as contrast beads or foams, among other examples, facilitate viewing of the medical device under ultrasonic imaging during insertion of the device and at any point while the device is implanted. One skilled in the art can readily determine an appropriate radiopaque and sonographic agent content to achieve the desired visibility. The polymer materials described may be mixed with the radiopaque and/or the sonographic agents above, or a colorant. A colorant may be used as a visual cue to a medical professional about the location of the medical device in the patient.

In variations of the embodiments described here or otherwise within the scope of the present disclosure, the filaments, including the radiopaque filaments, of the devices may be manufactured by weaving a plurality of filaments, for example, about the outer circumference of a mandrel in the shape of a medical device. The mandrel may be a specific jig for the desired architecture of the device. The mandrel may have portions extending radially from the tube that the filaments may be wound about to create the body of the device. One or more of these filaments could be a filament with higher radiopacity than the other filaments using the methods described above. Alternatively or in addition, one or more portions of the device and/or filaments may be treated for radiopacity as discussed above. The body may be heat treated for shape memory. The body may then be polished through abrasive particles to reduce micro-cracks and impurities from the surfaces of the device. Polishing of the device may be performed by electropolishing along with any type of media based treatments. A filament may be formed into coils by using a coil winder. Portions of filaments may be welded together and then adhered to a device.

Devices according to the embodiments described, and in accordance with other embodiments of the present disclosure, alone or in a system or kit or as part of a method or procedure, including with other accessories, may be used in cavities, lumens, tracts, vessels and organs of the body, such as procedures to drain, access or otherwise treat or diagnose conditions in the peritoneal, abdominal, bronchial or thoracic cavities, vascular vessels, gastrointestinal or urinary tract, uterus, bladder, lung and liver organs, etc.

Variations, modifications, and other implementations of the present disclosure in addition to the various embodiments described herein will occur to those of ordinary skill in the art. Accordingly, the present disclosure is to be defined not by the preceding illustrative description but instead by the following claims:

What is claimed is:

1. A medical device for placement within a lumen of a patient, the medical device comprising:
    a body having a length and a longitudinal axis along the length;
    a first radiopaque filament having a length and at least one radiopaque portion along the length, the radiopaque portion including a radiopaque material, and the first radiopaque filament outlining a first contour of the medical device; and
    a second radiopaque filament having a length and at least one radiopaque portion along the length, the radiopaque portion including a radiopaque material, and the second radiopaque filament outlining a second contour of the medical device;
    wherein the first radiopaque filament and the second radiopaque filament are circumferentially offset from each other about the longitudinal axis and circumferentially space apart the first contour from the second contour.

2. The medical device of claim 1, wherein the body comprises a plurality of filaments woven into a shape of the body of the medical device, the woven shape including the first contour and the second contour.

3. The medical device of claim 2, wherein the woven filaments are woven in a pattern and the first and second radiopaque filaments comprise circumferentially offset filaments within the pattern.

4. The medical device of claim 2, wherein the first radiopaque filament is disposed alongside one of the plurality of filaments.

5. The medical device of claim 1, wherein the second radiopaque filament is circumferentially offset from the first radiopaque filament by 90 degrees.

6. The medical device of claim 1, wherein the second radiopaque filament is circumferentially offset from the first radiopaque filament by 180 degrees.

7. The medical device of claim 1, wherein the body comprises an expandable member, and the first and second radiopaque filaments are disposed about an outer surface of the expandable member.

8. The medical device of claim 7, wherein the first and second radiopaque filaments are configured to expand and contract along with the outer surface of the expandable member.

9. A medical device for placement within a lumen of a patient, the medical device comprising:
    a body having a length and a longitudinal axis along the length;
    a first radiopaque filament having a length and at least one radiopaque portion along the length, the radiopaque portion including a radiopaque material, and the first radiopaque filament outlining a first contour of the medical device; and
    a second radiopaque filament having a length and at least one radiopaque portion along the length, the radiopaque portion including a radiopaque material, and the second radiopaque filament outlining a second contour of the medical device
    wherein the radiopaque portion of the first radiopaque filament has a first radiopacity value, the radiopaque portion of the second radiopaque filament has a second radiopacity value, and the first radiopacity value is different than the second radiopacity value.

10. The medical device of claim 1, wherein the radiopaque material is included in the radiopaque portion of the first and second radiopaque filaments by one or more of coating, impregnating, or cladding.

11. A medical device for placement within a lumen of a patient, the medical device comprising:
    a body comprising a plurality of woven filaments, at least two of the plurality of woven filaments comprising a radiopaque portion that includes a radiopaque material;
    wherein:

the plurality of woven filaments are woven in a pattern and with a shape that defines the body;

the at least two filaments comprising a radiopaque portion outline the body; and the at least two filaments comprising a radiopaque portion include at least one filament with a radiopacity value different from the radiopacity value of another filament.

12. The medical device of claim 11, wherein the at least two filaments comprising a radiopaque portion are offset from each other by 90 degrees circumferentially about a longitudinal axis of the medical device.

13. The medical device of claim 11, wherein the at least two filaments comprising a radiopaque portion are offset from each other by 180 degrees circumferentially about a longitudinal axis of the medical device.

14. The medical device of claim 11, wherein the body comprises an expandable member and the at least two filaments comprising a radiopaque portion are disposed about the expandable member.

15. The medical device of claim 11, wherein the at least two filaments comprising a radiopaque portion are disposed alongside one or more woven filaments that do not comprise a radiopaque portion.

16. The medical device of claim 11, wherein the at least two filaments comprising a radiopaque portion outline respective first and second contours that correspond to a desired orientation of the medical device when placed in the patient lumen.

17. The medical device of claim 11, wherein the at least two filaments comprising a radiopaque portion comprise a first filament that traces a first contour of the shape of the body and a second filament that traces a second contour of the shape of the body.

18. The medical device of claim 1, wherein the first radiopaque filament and the first contour identify a first orientation of the medical device, and the second radiopaque filament and the second contour identify a second orientation of the medical device differentiated from the first orientation.

19. The medical device of claim 1, wherein the first contour and the second contour correlate to different notable sections or features of the medical device.

20. The medical device of claim 11, wherein the at least two filaments comprising a radiopaque portion differentiate a first orientation of the body from a second orientation of the body.

* * * * *